(12) United States Patent
Hershey et al.

(10) Patent No.: US 10,471,260 B2
(45) Date of Patent: Nov. 12, 2019

(54) METHOD AND APPARATUS FOR CALIBRATING DORSAL HORN STIMULATION USING SENSORS

(71) Applicant: Boston Scientific Neuromodulation Corporation, Valencia, CA (US)

(72) Inventors: Bradley Lawrence Hershey, Valencia, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 334 days.

(21) Appl. No.: 14/856,364

(22) Filed: Sep. 16, 2015

(65) Prior Publication Data

US 2016/0082268 A1     Mar. 24, 2016

Related U.S. Application Data

(60) Provisional application No. 62/054,076, filed on Sep. 23, 2014.

(51) Int. Cl.
*A61N 1/36*     (2006.01)
*A61N 1/05*     (2006.01)

(52) U.S. Cl.
CPC ........ *A61N 1/36189* (2013.01); *A61N 1/0551* (2013.01); *A61N 1/36071* (2013.01); *A61N 1/36132* (2013.01); *A61N 1/36139* (2013.01)

(58) Field of Classification Search
CPC .......................... A61N 1/0551; A61N 1/36071
See application file for complete search history.

(56) References Cited

U.S. PATENT DOCUMENTS

| 5,540,730 A | 7/1996 | Terry, Jr. et al. |
| 6,516,227 B1 | 2/2003 | Meadows et al. |

(Continued)

FOREIGN PATENT DOCUMENTS

| AU | 2015321740 B2 | 6/2018 |
| WO | WO-2006029257 A2 | 3/2006 |

(Continued)

OTHER PUBLICATIONS

Rao, Prakash, et al., "Technique for Linking Electrodes Together During Programming of Neurostimulation System", U.S. Appl. No. 61/561,760, filed Nov. 18, 2011.

(Continued)

*Primary Examiner* — Michael J D Abreu
(74) *Attorney, Agent, or Firm* — Schwegman Lundberg & Woessner, P.A.

(57) ABSTRACT

An example of a system for applying neuromodulation to a patient includes a modulation output circuit and a modulation control circuit. The modulation output circuit may be configured to deliver dorsal horn stimulation. The modulation control circuit may be configured to control the delivery of the dorsal horn stimulation by executing a neuromodulation algorithm using modulation parameters. The modulation control circuit may include a response input and a parameter calibrator. The response input may be configured to receive response information indicative of one or more responses to the stimulation of the dorsal horn. The parameter calibrator may be configured to adjust one or more of the modulation parameters using the response information.

20 Claims, 11 Drawing Sheets

(56) References Cited

U.S. PATENT DOCUMENTS

| | | | |
|---|---|---|---|
| 6,675,046 B2 | 1/2004 | Holsheimer | |
| 6,871,099 B1 * | 3/2005 | Whitehurst | A61N 1/36071 607/46 |
| 6,895,280 B2 | 5/2005 | Meadows et al. | |
| 6,993,384 B2 | 1/2006 | Bradley et al. | |
| 7,317,948 B1 | 1/2008 | King et al. | |
| 7,333,857 B2 | 2/2008 | Campbell | |
| 7,539,538 B2 | 5/2009 | Parramon et al. | |
| 7,650,184 B2 | 1/2010 | Walter | |
| 7,801,619 B2 | 9/2010 | Gerber et al. | |
| 7,979,133 B2 | 7/2011 | Feler et al. | |
| 7,983,757 B2 | 7/2011 | Miyazawa et al. | |
| 8,019,439 B2 | 9/2011 | Kuzma et al. | |
| 8,224,453 B2 | 7/2012 | De Ridder | |
| 8,255,057 B2 | 8/2012 | Fang et al. | |
| 8,355,797 B2 | 1/2013 | Caparso et al. | |
| 8,380,318 B2 | 2/2013 | Kishawi et al. | |
| 8,455,716 B2 | 6/2013 | Huang et al. | |
| 8,504,147 B2 | 8/2013 | Deem et al. | |
| 8,615,300 B2 | 12/2013 | Feler et al. | |
| 8,649,874 B2 * | 2/2014 | Alataris | A61N 1/36071 607/116 |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,706,240 B2 | 4/2014 | Bradley et al. | |
| 8,731,675 B2 | 5/2014 | Ranu et al. | |
| 8,751,009 B2 | 6/2014 | Wacnik | |
| 2003/0139781 A1 | 7/2003 | Bradley et al. | |
| 2005/0055065 A1 * | 3/2005 | Campbell | A61N 1/36071 607/46 |
| 2007/0150036 A1 | 6/2007 | Anderson | |
| 2008/0188909 A1 | 8/2008 | Bradley | |
| 2009/0157141 A1 | 6/2009 | Chiao et al. | |
| 2009/0204173 A1 | 8/2009 | Fang et al. | |
| 2009/0270960 A1 * | 10/2009 | Zhao | A61N 1/0551 607/117 |
| 2010/0010566 A1 | 1/2010 | Thacker et al. | |
| 2010/0121409 A1 | 5/2010 | Kothandaraman et al. | |
| 2010/0249875 A1 | 9/2010 | Kishawi et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2012/0059446 A1 | 3/2012 | Wallace et al. | |
| 2012/0083709 A1 | 4/2012 | Parker et al. | |
| 2012/0150257 A1 | 6/2012 | Aur et al. | |
| 2012/0253422 A1 | 10/2012 | Thacker et al. | |
| 2012/0265279 A1 | 10/2012 | Zhu et al. | |
| 2012/0283797 A1 | 11/2012 | De Ridder | |
| 2012/0290041 A1 | 11/2012 | Kim et al. | |
| 2013/0066411 A1 | 3/2013 | Thacker et al. | |
| 2013/0116752 A1 | 5/2013 | Parker et al. | |
| 2013/0268021 A1 | 10/2013 | Moffitt | |
| 2013/0296975 A1 | 11/2013 | Lee et al. | |
| 2014/0005744 A1 | 1/2014 | Hershey et al. | |
| 2014/0081346 A1 | 3/2014 | Eguibar et al. | |
| 2014/0081349 A1 | 3/2014 | Lee et al. | |
| 2014/0236257 A1 * | 8/2014 | Parker | A61B 5/04001 607/46 |
| 2014/0243926 A1 | 8/2014 | Carcieri | |
| 2014/0277267 A1 | 9/2014 | Vansickle et al. | |
| 2015/0151125 A1 * | 6/2015 | Zhu | A61N 1/36071 607/46 |

FOREIGN PATENT DOCUMENTS

| | | |
|---|---|---|
| WO | WO-2006135791 A2 | 12/2006 |
| WO | WO-2013141996 A1 | 9/2013 |
| WO | WO-2016048756 A1 | 3/2016 |

OTHER PUBLICATIONS

Vansickle, Dennis Allen, et al., "Neuromodulation System and Method for Transitioning Between Programming Modes", U.S. Appl. No. 14/214,752, filed Mar. 15, 2014.

Vansickle, Dennis Allen, "Systems and Methods for Delivering Sub-Threshold Therapy to a Patient", U.S. Appl. No. 61/801,917, filed Mar. 15, 2013.

"International Application Serial No. PCT/US2015/50447, International Search Report dated Nov. 25, 2015", 5 pgs.

"International Application Serial No. PCT/US2015/50447, Written Opinion dated Nov. 25, 2015", 6 pgs.

"International Application Serial No. PCT/US2015/050447, International Preliminary Report on Patentability dated Apr. 6, 2017", 8 pgs.

"Australian Application Serial No. 2015321740, First Examination Report dated Oct. 6, 2017", 3 pgs.

"European Application Serial No. 15771406.4, Response filed Dec. 13, 2017 to Communication Pursuant to Rules 161 and 162 EPC dated Jun. 7, 2017", 12 pgs.

"Australian Application Serial No. 2015321740, Response filed Feb. 8, 2018 to First Examination Report dated Oct. 6, 2017", 13 pgs.

"Japanese Application Serial No. 2017-516051, Office Action dated Mar. 26, 2018", w/ English translation, 4 pgs.

* cited by examiner

METHOD AND APPARATUS FOR CALIBRATING DORSAL HORN STIMULATION USING SENSORS

CLAIM OF PRIORITY

This application claims the benefit of provisional U.S. patent application Ser. No. 62/054,076, filed on Sep. 23, 2014, which is hereby incorporated by reference in its entirety.

TECHNICAL FIELD

This document relates generally to neuromodulation and more particularly to a method and system for dorsal horn stimulation with feedback control using one or more sensed responses to the stimulation.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes. Some neural targets may be complex structures with different types of nerve fibers. An example of such a complex structure is the neuronal elements in and around the spinal cord targeted by SCS.

SUMMARY

An example (e.g. "Example 1) of a system for applying neuromodulation to a patient includes a modulation output circuit and a modulation control circuit. The patient has a nervous system including a dorsal horn, a dorsal root, and a dorsal column. The modulation output circuit may be configured to deliver dorsal horn stimulation to the dorsal horn. The modulation control circuit may be configured to control the delivery of the dorsal horn stimulation by executing a neuromodulation algorithm using a plurality of modulation parameters. The modulation control circuit may include a response input and a parameter calibrator. The response input may be configured to receive response information indicative of one or more responses to the stimulation of the dorsal horn. The parameter calibrator may be configured to adjust one or more modulation parameters of the plurality of modulation parameters using the response information.

In Example 2, the subject matter of claim 1 may optionally be configured such that the modulation control circuit is configured to control the delivery of the dorsal horn stimulation by executing a neuromodulation algorithm for delivering sub-perception dorsal horn stimulation. The sub-perception dorsal horn stimulation is to selectively stimulate the dorsal horn over the dorsal column.

In Example 3, the subject matter of any one or any combination of Examples 1 and 2 may optionally be configured such that the response input is configured to receive the response information including one or more response parameters each being a quantitative measure of a response of the one or more responses to the dorsal horn stimulation, and the parameter calibrator is configured to adjust the one or more modulation parameters of the plurality of modulation parameters to maintain the one or more response parameters within a target value range.

In Example 4, the subject matter of Example 3 may optionally be configured to further include one or more sensors and a parameter generator. The one or more sensors may be configured to sense one or more neurophysiological signals each indicative of a physiological function associated with pain. The parameter generator may be configured to derive the one or more response parameters from the one or more neurophysiological signals.

In Example 5, the subject matter of Example 3 may optionally be configured such that the modulation output circuit is further configured to deliver dorsal root stimulation to the dorsal root, the modulation control circuit is configured to control the delivery of the dorsal horn stimulation and control the delivery of the dorsal root stimulation by executing a testing algorithm for delivering the dorsal horn stimulation interleaved with the dorsal root stimulation, and further comprising a sensor configured to sense a response to the dorsal root stimulation in the dorsal column, the response modulated by the dorsal horn stimulation.

In Example 6, the subject matter of Example 5 may optionally be configured such that the sensor is configured to sense local field potentials (LFPs) in axons in the dorsal column, and the parameter generator is configured to derive one or more parameters of the one or more response parameters from the sensed LFPs.

In Example 7, the subject matter of Example 5 may optionally be configured such that the sensor is configured to sense evoked compound action potentials (eCAPs) in axons in the dorsal column, and the parameter generator is configured to derive one or more parameters of the one or more response parameters from the sensed eCAPs.

In Example 8, the subject matter of any one or any combination of Examples 1-7 may optionally be configured to include an implantable modulation device including the modulation output circuit, the response input, and the modulation control circuit, and further include a monitoring device configured monitor the one or more responses to the dorsal horn stimulation and produce the response information.

In Example 9, the subject matter of Example 8 may optionally be configured such that the monitoring device c includes an implantable monitoring device.

In Example 10, the subject matter of Example 8 may optionally be configured such that the monitoring device includes a portable monitoring device.

In Example 11, the subject matter of Example 10 may optionally be configured such that the monitoring device includes a wearable monitoring device.

In Example 12, the subject matter of any one or any combination of Examples 8-11 may optionally be configured such that the implantable modulation device is communicatively coupled to the monitoring device via a wireless link.

In Example 13, the subject matter of Example 8 may optionally be configured such that the monitoring device is integrated into the implantable modulation device.

In Example 14, the subject matter of Example 8 may optionally be configured such that the monitoring device is configured to perform one or more of quantitative sensory testing, electroencephalography (EEG), electrocorticography (ECoG), diffuse optical imaging, and functional magnetic resonance imaging (fMRI).

In Example 15, the subject matter of any one or any combination of Examples 1-14 may optionally be configured such that the modulation output circuit is configured to deliver electrical pulses to the dorsal horn.

An example of a method (e.g. "Example 16") for applying neuromodulation to a patient having a nervous system including a dorsal horn, a dorsal root, and a dorsal column is provided. The method may include delivering dorsal horn stimulation to the dorsal horn, controlling the delivery of the dorsal horn stimulation by executing a neuromodulation algorithm using a plurality of modulation parameters, receiving response information indicative of one or more responses to the dorsal horn stimulation, and adjusting one or more modulation parameters of the plurality of modulation parameters using the response information.

In Example 17, the subject matter of executing the neuromodulation algorithm as found in Example 16 may optionally include executing a neuromodulation algorithm for delivering sub-perception dorsal horn stimulation. The sub-perception dorsal horn stimulation is to selectively stimulate the dorsal horn over the dorsal column.

In Example 18, the subject matter of delivering the stimulation to the dorsal horn as found in any one or any combination of Examples 16 and 17 may optionally include delivering the dorsal horn stimulation from an implantable device.

In Example 19, the subject matter of any one or any combination of Examples 16-18 may optionally further include sensing one or more neurophysiological signals and deriving one or more response parameters of the response information from the one or more neurophysiological signals. The one or more response parameters are each a quantitative measure of a response of the one or more responses to the dorsal horn stimulation.

In Example 20, the subject matter of sensing the one or more neurophysiological signals as found in Example 19 may optionally include performing one or more of quantitative sensory testing, electroencephalography (EEG), electrocorticography (ECoG), diffuse optical imaging, and functional magnetic resonance imaging (fMRI).

In Example 21, the subject matter of adjusting one or more modulation parameters of the plurality of modulation parameters as found in any one or any combination of Examples 19 and 20 may optionally include adjusting the one or more modulation parameters of the plurality of modulation parameters to maintain the one or more response parameters within a target value range.

In Example 22, the subject matter of deriving the one or more response parameters as found in any one or any combination of Examples 19-22 may optionally include deriving one or more response parameters each indicative of a physiological function associated with pain.

In Example 23, the subject matter of claim 19 may optionally further include delivering dorsal root stimulation to the dorsal root, and controlling the delivery of the dorsal horn stimulation and the delivery of the dorsal root stimulation such that the dorsal horn stimulation is interleaved with the dorsal root stimulation. The subject matter of sensing the one or more neurophysiological signals as found in Example 19 may optionally include sensing a response to the dorsal root stimulation in axons in the dorsal column modulated by the dorsal horn stimulation during the delivery of the dorsal horn stimulation interleaved with the dorsal root stimulation.

In Example 24, the subject matter of sensing the response to the dorsal root stimulation in axons in the dorsal column as found in Example 23 may optionally include sensing local field potentials (LFPs) in axons in the dorsal column.

In Example 25, the subject matter of sensing the response to the dorsal root stimulation in axons in the dorsal column as found in Example 23 may optionally include sensing evoked compound action potentials (eCAPs) in axons in the dorsal column.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 10 illustrates a schematic view of the electrical modulation lead showing an example of the fractionalization of the anodic current delivered to the electrodes on the electrical modulation lead.

FIG. 11 illustrates, by way of example, a schematic illustration of a gradient in the longitudinal direction along the axis of the electrical modulation lead.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
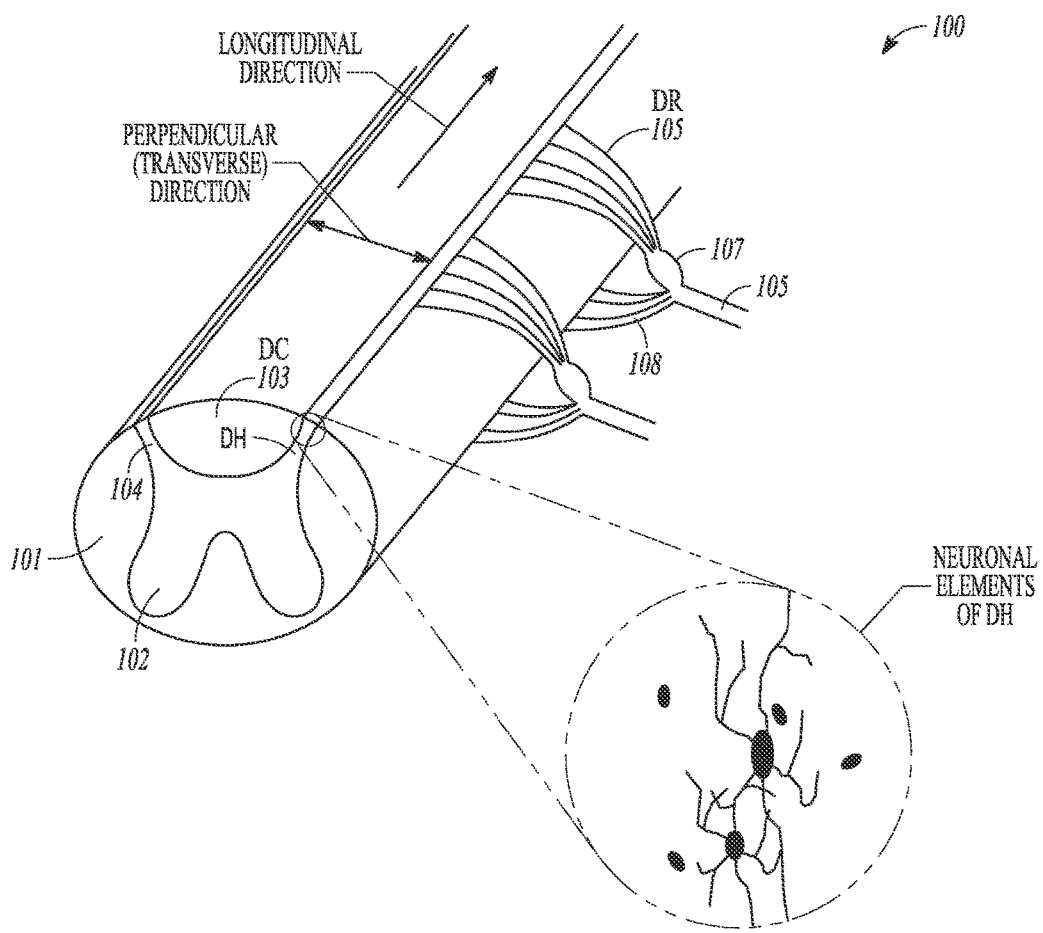
FIG. 1 illustrates a portion of a spinal cord.

Various embodiments described herein involve spinal cord modulation. A brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example, but the patient does not sense the delivery of the modulation field (e.g. paresthesia). Sub-perception therapy may include higher frequency modulation (e.g. about 1500 Hz or above) of the spinal cord that effectively blocks the transmission of pain signals in the afferent fibers in the DC. Some embodiments herein selectively modulate DH tissue or DR tissue over DC tissue to provide sub-perception therapy. Such selective modulation is not delivered at these higher frequencies. For example, the selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

Figure 2:
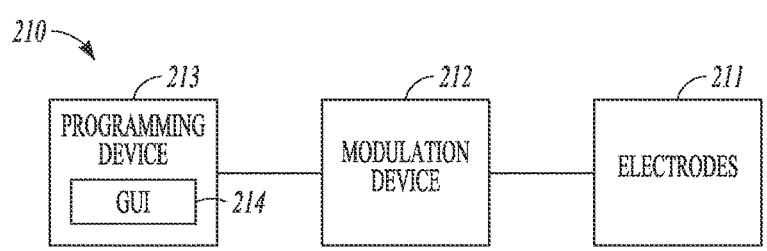
FIG. 2 illustrates, by way of example, an embodiment of a neuromodulation system.

FIG. 2 illustrates an embodiment of a neuromodulation system. The illustrated system 210 includes electrodes 211, a modulation device 212, and a programming device 213. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters, such as modulation parameters specifying the electrical pulses and a selection of electrodes through which each of the electrical pulses is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
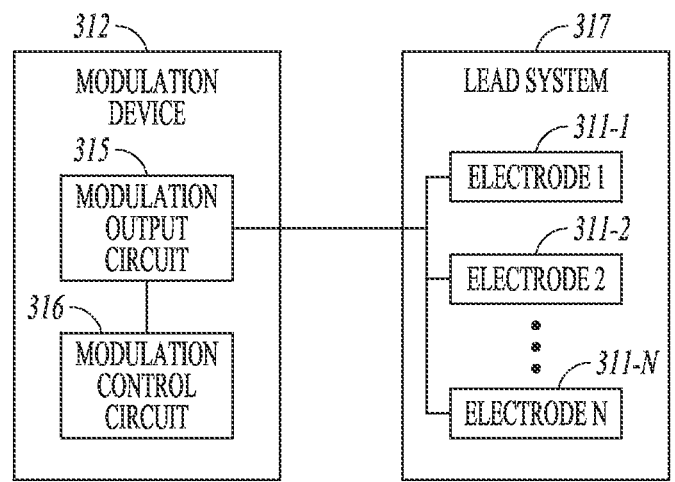
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers neuromodulation pulses. The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient, where N≥2. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical pulses, presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

Conventional programming for SCS therapy uses paresthesia to select an appropriate modulation parameter set. The paresthesia induced by the modulation and perceived by the patient should be located in approximately the same place in the patient's body as the pain that is the target of treatment. When leads are implanted within the patient, an operating room (OR) mapping procedure may be performed to apply electrical modulation to test placement of the leads and/or electrodes, thereby assuring that the leads and/or electrodes are implanted in effective locations within the patient.

Once the leads are correctly positioned, a fitting procedure, which may be referred to as a navigation session, may be performed to program the external control device, and if applicable the neuromodulation device, with a set of modulation parameters that best addresses the painful site. Thus, the navigation session may be used to pinpoint the volume of activation (VOA) or areas correlating to the pain. The procedure may be implemented to target the tissue during implantation, or after implantation should the leads gradually or unexpectedly move that would otherwise relocate the modulation energy away from the target site. By reprogramming the neuromodulation device (typically by independently varying the modulation energy on the electrodes), the VOA can often be moved back to the effective pain site without having to re-operate on the patient in order to reposition the lead and its electrode array. When adjusting the VOA relative to the tissue, it is desirable to make small changes in the proportions of current, so that changes in the spatial recruitment of nerve fibers will be perceived by the patient as being smooth and continuous and to have incremental targeting capability.

Figure 4:
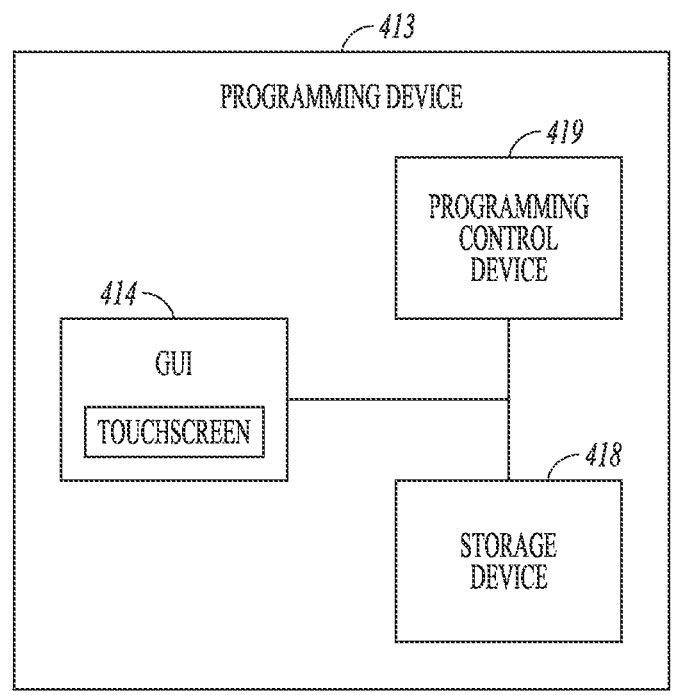
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The programming device 413 may transmit the plurality of modulation parameters to the modulation device. In some embodiments, the programming device 413 may transmit power to the modulation device. The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
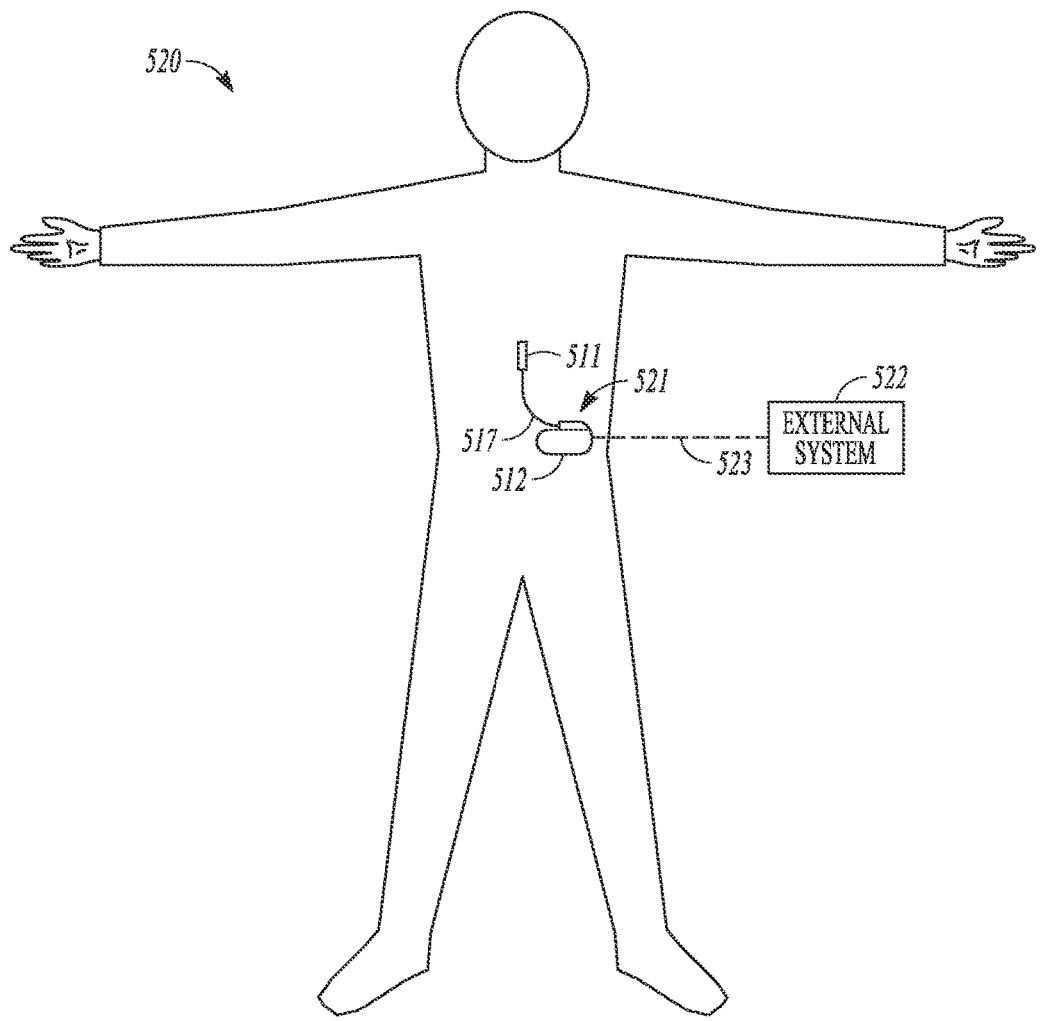
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable modulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
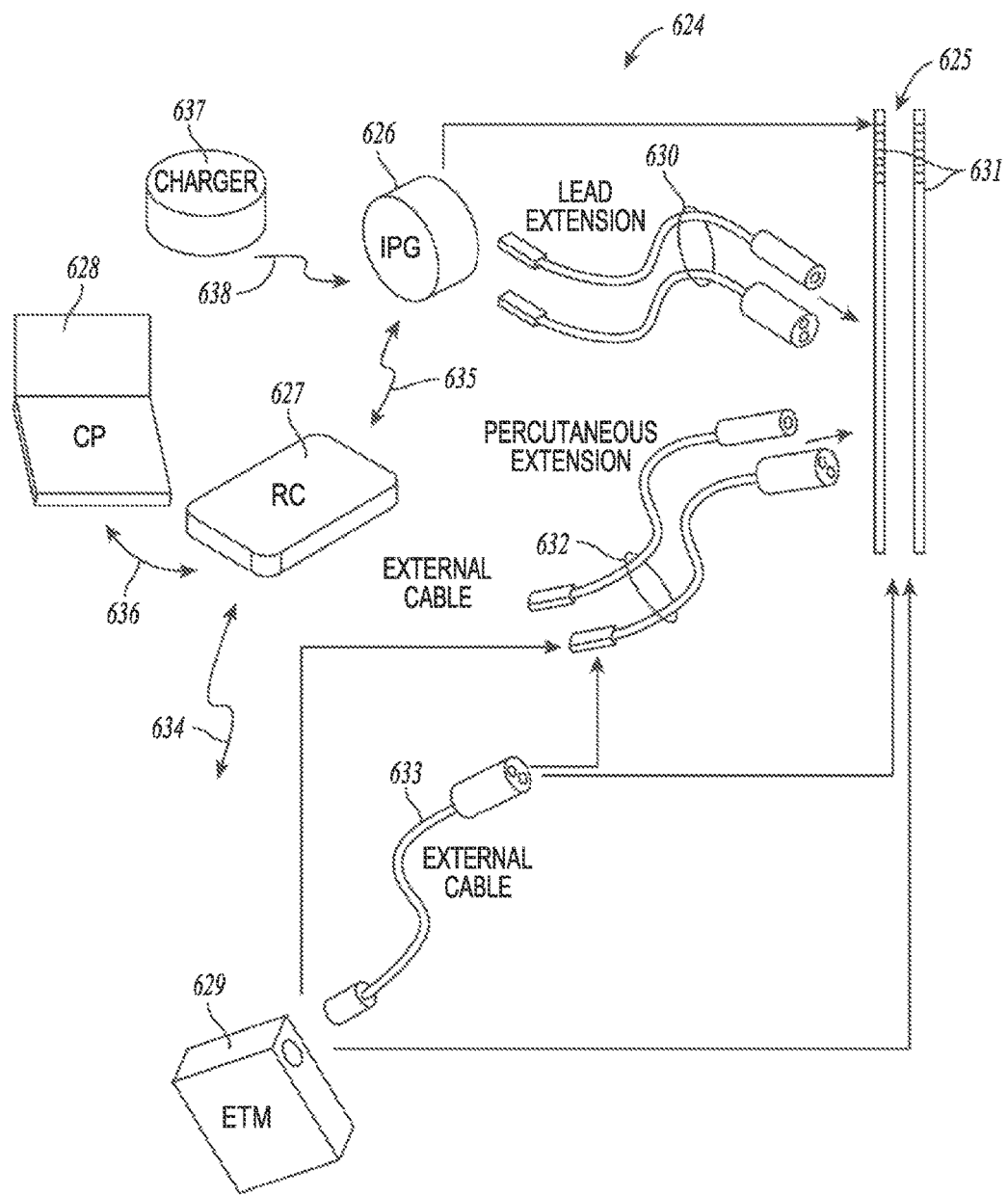
FIG. 6 illustrates, by way of example, an embodiment of a Spinal Cord Stimulation (SCS) system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 624 may generally include a plurality (illustrated as two) of implantable neuromodulation leads 625, an implantable pulse generator (IPG) 626, an external remote controller RC 627, a clinician's programmer (CP) 628, and an external trial modulator (ETM) 629. The IPG 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 626 includes pulse generation circuitry that delivers electrical modulation energy in the form of a pulsed electrical waveform (i.e., a temporal series of electrical pulses) to the electrodes in accordance with a set of modulation parameters.

The ETM 629 may also be physically connected via the percutaneous lead extensions 632 and external cable 633 to the neuromodulation leads 625. The ETM 629 may have similar pulse generation circuitry as the IPG 626 to deliver electrical modulation energy to the electrodes accordance with a set of modulation parameters. The ETM 629 is a non-implantable device that is used on a trial basis after the neuromodulation leads 625 have been implanted and prior to implantation of the IPG 626, to test the responsiveness of the modulation that is to be provided. Functions described herein with respect to the IPG 626 can likewise be performed with respect to the ETM 629.

The RC 627 may be used to telemetrically control the ETM 629 via a bi-directional RF communications link 634. The RC 627 may be used to telemetrically control the IPG 626 via a bi-directional RF communications link 635. Such control allows the IPG 626 to be turned on or off and to be programmed with different modulation parameter sets. The IPG 626 may also be operated to modify the programmed modulation parameters to actively control the characteristics of the electrical modulation energy output by the IPG 626. A clinician may use the CP 628 to program modulation parameters into the IPG 626 and ETM 629 in the operating room and in follow-up sessions.

The CP 628 may indirectly communicate with the IPG 626 or ETM 629, through the RC 627, via an IR communications link 636 or other link. The CP 628 may directly communicate with the IPG 626 or ETM 629 via an RF communications link or other link (not shown). The clinician detailed modulation parameters provided by the CP 628 may also be used to program the RC 627, so that the modulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical modulation generated by the IPG 626 to allow the desired parameters to be determined based on patient feedback or other feedback and for subsequently programming the IPG 626 with the desired modulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting.

An external charger 637 may be a portable device used to transcutaneously charge the IPG via a wireless link such as an inductive link 638. Once the IPG has been programmed, and its power source has been charged by the external charger or otherwise replenished, the IPG may function as programmed without the RC or CP being present.

Figure 7:
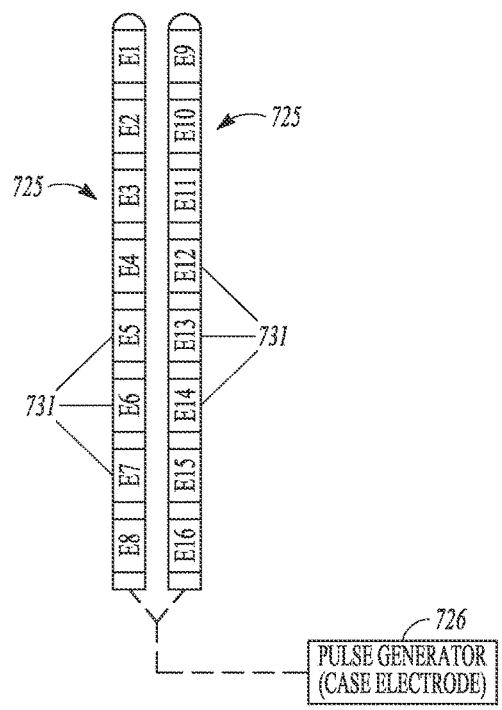
FIG. 7 illustrates, by way of example, some features of the neuromodulation leads and a pulse generator.

FIG. 7 illustrates, by way of example, some features of the neuromodulation leads 725 and a pulse generator 726. The pulse generator 726 may be an implantable device (IPG) or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by IPG. Electrical modulation energy is provided to the electrodes in accordance with a set of modulation parameters programmed into the pulse generator. The electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the IPG case. The system may be capable of transmitting modulation energy to the tissue in a monopolar or multipolar (e.g., bipolar, tripolar, etc.) fashion. Monopolar modulation occurs when a selected one of the lead electrodes is activated along with the case of the IPG, so that modulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The IPG may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

FIGS. 8-11 illustrate, by way of example, a difference in electrical field strength in the longitudinal and transverse directions when the current is fractionalized such that the electrical field in the longitudinal direction generated by the fractionalized current delivered to each electrode is approximately equal. The voltage at a patient's spinal cord (especially at the DC fibers) is approximately equal in the longitudinal direction, resulting in a voltage gradient of approximately zero along the DC. This may require different amounts of fractionalized current delivered to each electrode. Calibration techniques are used to determine the proper current fractionalization. With the current fractionalized to a plurality of electrodes on the electrical modulation lead, the resulting field can be calculated by superimposing the fields generated by the current delivered to each electrode. Moreover each electrical field has a longitudinal component and a transverse component.

Figures 8, 9:
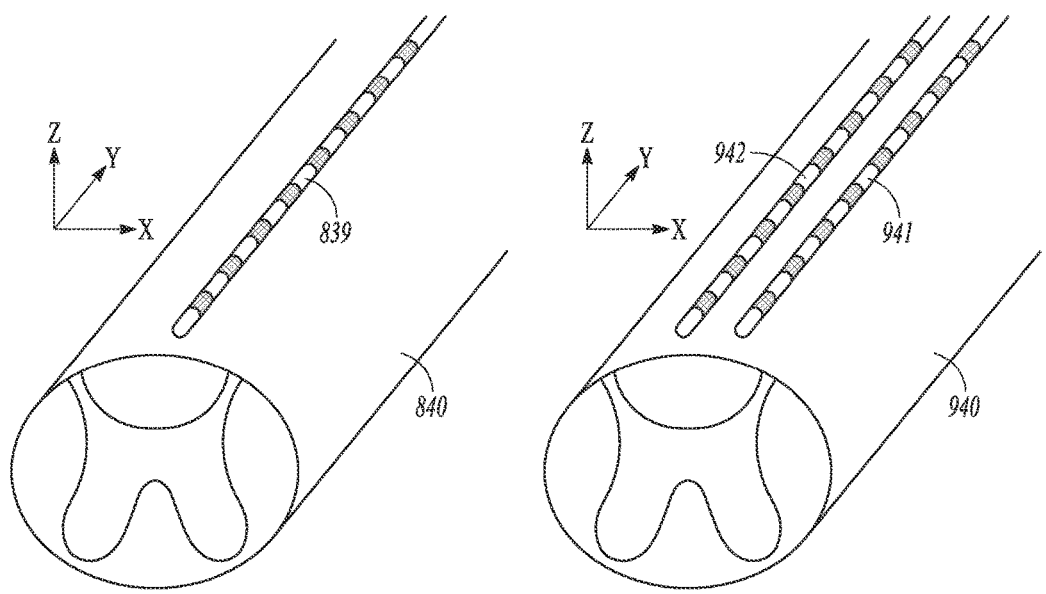
FIGS. 8-11 illustrate, by way of example, a difference in electrical field strength in the longitudinal and transverse directions when the current is fractionalized such that the electrical field in the longitudinal direction generated by the fractionalized current delivered to each electrode is approximately equal.

FIG. 8 is a schematic view of a single electrical modulation lead 839 implanted over approximately the longitudinal midline of the patient's spinal cord 840. It is understood that additional leads or lead paddle(s) may be used, such as may be used to provide a wider electrode arrangement and/or to provide the electrodes closer to dorsal horn elements, and that these electrode arrays also may implement fractionalized current. FIG. 9 illustrates an embodiment where an electrical modulation lead 941 has been implanted more laterally with respect to the spinal cord, thereby placing it proximate the dorsal horn of the spinal cord, and the other electrical modulation lead 942 has been implanted more medially with respect to the spinal cord, thereby placing it proximate the dorsal column of the spinal cord 940. Placement of the lead more proximate to the DH than the DC may be desirable to preferentially stimulate DH elements over DC neural elements for a sub-perception therapy. Any other plurality of leads or a multiple column paddle lead can also be used. Longitudinal component of the electrical field is directed along the y-axis depicted in FIG.

8, and a transverse component of the electrical field is directed along the x-axis depicted in FIG. 8.

Figure 10:
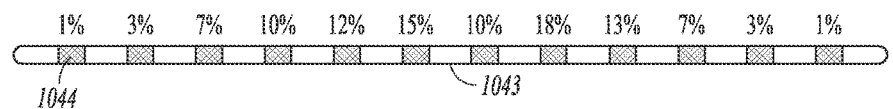

FIG. 10 is a schematic view of the electrical modulation lead 1043 showing an example of the fractionalization of the anodic current delivered to the electrodes on the electrical modulation lead. These figures illustrate fractionalization using monopolar modulation where a case electrode of the IPG is the only cathode, and carries 100% of the cathodic current. The fractionalization of the anodic current shown in FIG. 10 does not deliver an equal amount of current to each electrode 1044, because this embodiment takes into account electrode/tissue coupling differences, which are the differences in how the tissue underlying each electrode reacts to electrical modulation. Also, the ends of the portion of the electrical modulation lead include electrodes having lower gradient in the longitudinal direction. The magnitude of the electrical field tapers down at the ends of the electrical modulation lead. Fractionalization of the current to the electrodes is controlled such that the tissue underlying each electrode in the middle portion of the electrical modulation lead reacts approximately equally to the electrical modulation, or tissue activation underlying each electrode are eliminated. However, the resulting fractionalization is not equal. In the embodiment shown in FIG. 10, fractionalization of the current to the middle electrodes varies from 10% to 18%, reflecting the variation in the tissue underlying those electrodes. The fractionalization across the electrical modulation lead can vary in any manner as long as the total of fractionalized currents equals 100%. Various embodiments described herein implement a programmed algorithm to determine the appropriate fractionalization to achieve a desired modulation field property (e.g. constant electric field, or constant electric field magnitude, or constant voltage).

Figure 11:
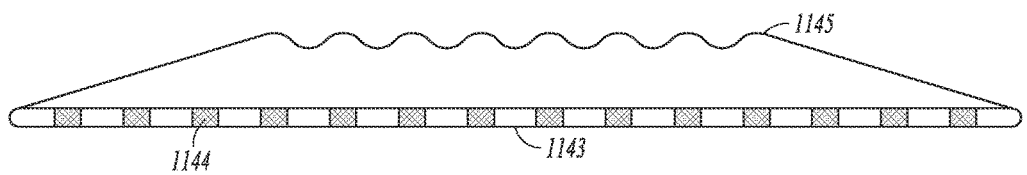

FIG. 11 illustrates, by way of example, a schematic illustration of a gradient in the longitudinal direction along the axis of the electrical modulation lead. The electrical field strength 1145 in the longitudinal direction is plotted over a schematic representation of the electrodes 1144 on the electrical modulation lead 1143. The illustration in FIG. 11 shows that the electrical field strength is substantially constant over the middle portion of the electrical modulation lead, but may form a wave with very small amplitude because of the gaps between the electrodes in the lead. This substantially constant electrical field forms a small longitudinal gradient, which minimizes activation of the large myelinated axons in the dorsal column. The illustration in FIG. 11 also shows the electrical field in the longitudinal direction tapering at the ends of the electrical modulation lead.

Figure 12:
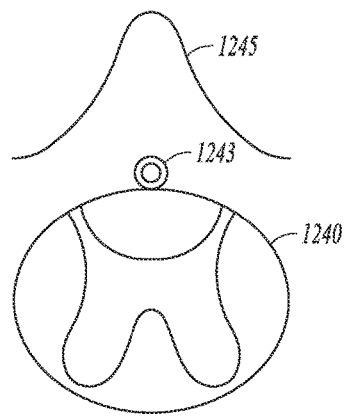
FIG. 12 illustrates, by way of example, a schematic illustration of a gradient in the transverse direction.
Figure 13A:
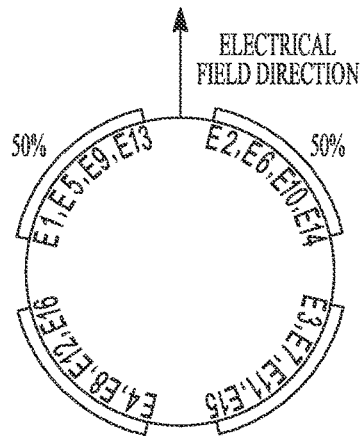
FIGS. 13A-13C and 14A-14C illustrate, by way of example, neural modulation leads in which the electrodes may take the form of segmented electrodes that are circumferentially and axially disposed about the neuromodulation leads.
Figure 13B:
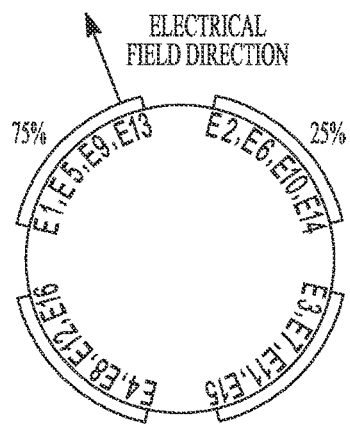
Figure 13C:
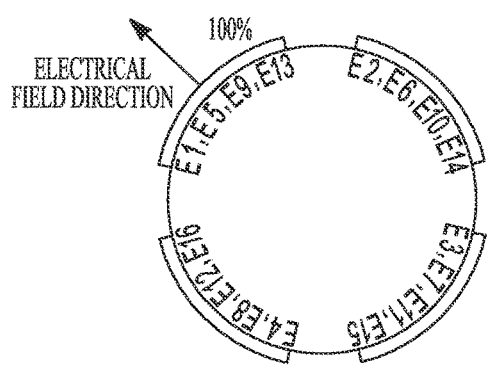
Figure 14A:
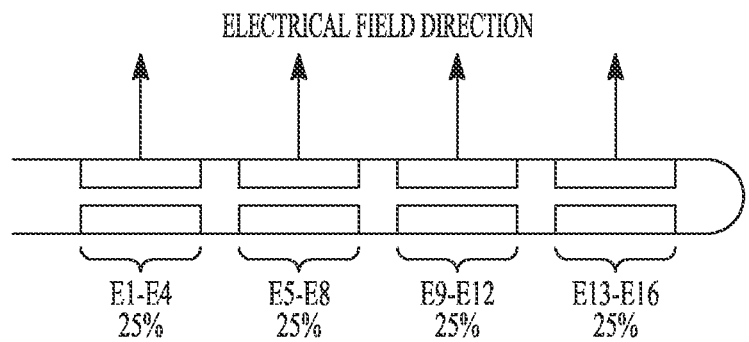
Figure 14B:
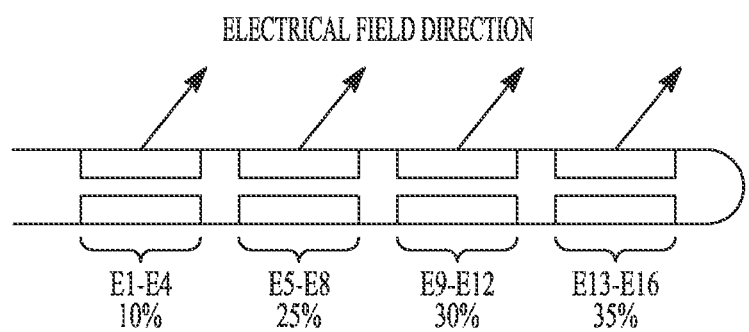
Figure 14C:
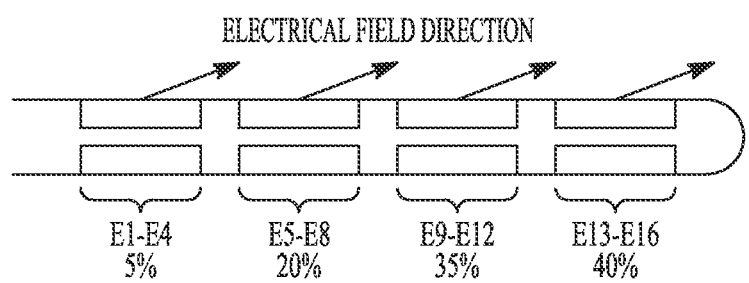

FIG. 12 illustrates, by way of example, a schematic illustration of a gradient in the transverse direction. The transverse electrical field strength 1245 in the transverse direction is plotted over a schematic representation of the electrical modulation lead 1243 and the spinal cord 1240 of the patient. The illustration in FIG. 12 shows that the transverse electrical field strength is greatest adjacent the electrical modulation lead and falls off lateral of the electrical modulation lead. Use of additional modulation leads to widen the electrode array may be used to provide desired fractionalization to also provide a region of a substantially constant electric field for a distance along the transverse direction. Substantially constant electric fields favor modulation of dorsal horn and/or dorsal root neuronal elements over dorsal column neuronal elements.

FIGS. 13A-13C and 14A-14C illustrate, by way of example, neural modulation leads in which the electrodes may take the form of segmented electrodes that are circumferentially and axially disposed about the neuromodulation leads. By way of non-limiting example, each neuromodulation lead may carry sixteen electrodes, arranged as four rings of electrodes (the first ring consisting of electrodes E1-E4; the second ring consisting of electrodes E5-E8; the third ring consisting of electrodes E9-E12; and the fourth ring consisting of electrodes E13-E16) or four axial columns of electrodes (the first column consisting of electrodes E1, E5, E9, and E13; the second column consisting of electrodes E2, E6, E10, and E14; the third column consisting of electrodes E3, E7, E11, and E15; and the fourth column consisting of electrodes E4, E8, E12, and E16). The actual number and shape of leads and electrodes may vary according to the intended application.

The SCS system may be used to deliver electrical energy to the spinal cord of the patient using electrical fields having different orientations, also as generally illustrated in FIGS. 13A-13C and 14A-14C. The orientation of the electrical field may be selected to target the different directions/orientations of the DH elements. To generate electrical fields in different medio-lateral directions, the electrodes may have different current fractionalizations in the radial direction. Although it is desirable that the electrical fields preferentially stimulate DH and/or DR elements over the DC elements, as discussed above, the electrical fields may still be oriented in different rostro-caudal directions (i.e., the direction of the electrical fields as projected on a longitudinal plane through the spinal cord), although preferably not in an orientation that will result in the perception of paresthesia. To generate electrical fields in different rostro-caudal directions, the electrodes may have different current fractionalizations in the longitudinal direction.

The SCS system may be configured to deliver different electrical fields to achieve a temporal summation of modulation in the DH elements. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

An embodiment modifies the fractionalized current delivered to each electrode to minimize the electrical field gradient in the longitudinal direction, so as to minimize activation of the DC elements. Minimizing activation of the DC elements can include a model-based calculation, where the model includes the information from the calibration. A discrete activating function can be calculated by the formula: $AF(n) = G_a/(\pi \times d \times l) \times [V_e(n-1) - 2V_e(n) + V_e(n+1)]$, wherein $G_a$ is the axonal intermodal conductance, d is the axonal diameter, l is the length of the node of Ranvier, $V_e(n)$ is the strength of the electric field at the node for which the activating function is determined, $V_e(n-1)$ is the strength of the electric field at the node preceding the node for which the activating function is determined, and $V_e(n+1)$ is the strength of the electric field at the node following the node for which the activating function is determined. Using this formula, the discrete activating function is calculated from the conductance normalized to the surface area of the node of Ranvier.

Modulation thresholds vary from patient to patient and from electrode to electrode within a patient. An electrode/tissue coupling calibration of the electrodes may be performed to account for these different modulation thresholds and provide a more accurate fractionalization of the current between electrodes. For example, perception threshold may be used to normalize the electrodes. The RC or the CP may be configured to prompt the patient to actuate a control element, once paresthesia is perceived by the patient. In response to this user input, the RC or the CP may be configured to respond to this user input by storing the modulation signal strength of the electrical pulse train delivered when the control element is actuated. Other sensed parameter or patient-perceived modulation values (e.g. constant paresthesia, or maximum tolerable paresthesia) may be used to provide the electrode/tissue coupling calibration of the electrodes. These sensed parameter or patient-perceived modulation values may be used to estimate the current fractionalization by minimizing the sum of the square of the discrete activating function divided by the determined value (e.g. perception threshold) at each electrode on an electrical modulation lead. Squaring the discrete activating function, or any driving force from the electrical field, eliminates the differences in depolarizing and hyperpolarizing fields. The current fractionalization that results in a minimize sum minimizes the field gradient in the longitudinal direction.

FIGS. 15-19 illustrate, by way of example, various embodiments of neuromodulation method and apparatus for closed-loop dorsal horn stimulation (DHS). DHS has been applied for pain management. Optimization of DHS in existing neuromodulation systems is performed manually and only involves capturing monopolar paresthesia thresholds. Recalibration of the DHS parameters is performed manually and requires subjective input from the patient receiving DHS. Various embodiments of the present subject matter provide objective input, such as various physiological responses detectable from the patient, for use as feedback in adjustment or optimization of DHS parameters. Various embodiments monitor neurophysiological signals that are quantitatively indicative of modulation of an physiological effect being the goal of electrical neuromodulation, such as monitoring one or more signals known to be associated with pain in a DHS system. DHS may work by directly modulating the pre-synaptic or post-synaptic membrane of neural networks in the dorsal horn (DH). These networks involve inputs from the dorsal roots (DR) and project through many fiber tracts, the dorsal columns (DC), and the lateral spinothalamic tract, among others. Some processing of signals occurs in the DH. Thus, various embodiments calibrate DHS parameters providing interleaved DHS and stimulation of DR afferents while measuring evoked response in the DC. Optimization of the DHS parameters is performed by monitoring the modulation of the transfer function between the DR and the DC resulting from the DHS.

Figure 15:
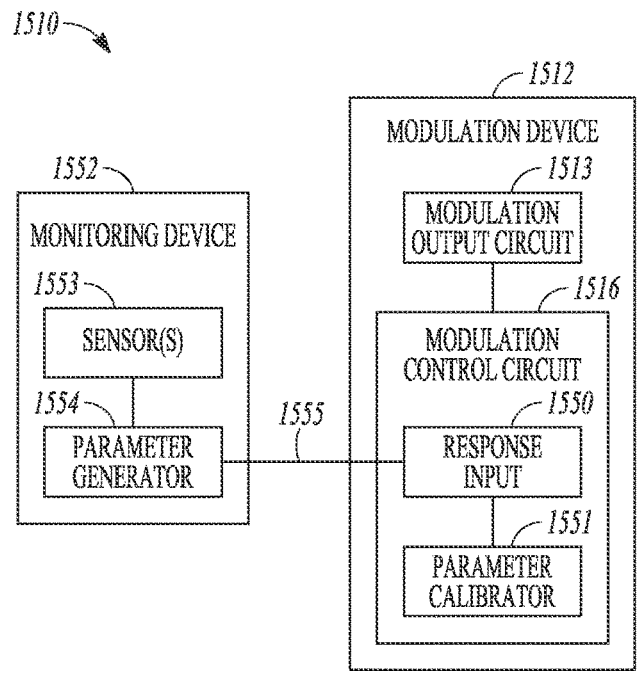
FIG. 15 illustrates, by way of example, an embodiment of a neuromodulation system for closed-loop dorsal horn stimulation.

FIG. 15 illustrates, by way of example, an embodiment of a neuromodulation system 1510 for closed-loop DHS. The system 1510 includes a modulation device 1512 and a monitoring device 1552. In various embodiments, the system 1510 may be an implantable neuromodulation system. In one embodiment, the system 1510 is implemented in implantable neuromodulation system 520, with the modulation device 1512 being implemented in implantable modulation device 512 and the monitoring device 1552 being implemented in the external system 522. In another embodiment, the modulation device 1512 and the monitoring device 1552 are each an implantable device, thus allowing the closed-loop DHS to be automatically performed in a totally implantable system. In another embodiment, the modulation device 1512 and the monitoring device 1552 are integrated into an implantable device such as an example of implantable modulation device 512, thus allowing the closed-loop DHS to be automatically performed in one implantable neuromodulation device.

In the illustrated embodiment, the modulation device 1512 includes a modulation output circuit 1513 and a modulation control circuit 1516. The modulation output circuit 1513 delivers the DHS to the DH. In various embodiments, the modulation output circuit 1513 is a multi-channel device capable of delivering stimulation to a plurality of target sites, such as the DH and DR as further discussed below. In various embodiments, the modulation output circuit 1513 delivers the stimulation (modulation) in the form of electrical pulses.

The modulation control circuit 1516 controls the delivery of the DHS pulses using a plurality of modulation parameters. Examples of the modulation parameters include, but are not limited to, number of contacts (electrodes) used to deliver the electrical pulses, breadth of the contact span, electrical current distribution, pulse amplitude, pulse width, pulse frequency/interpulse interval, duty cycle, and pulse waveform. In various embodiments, the modulation control circuit 1516 is configured to execute a neuromodulation algorithm for pain management using the DHS. In one embodiment, the modulation output circuit 1513 is also configured to execute a testing algorithm for delivering the DHS interleaved with the dorsal root stimulation (DRS) that includes delivering stimulation to the DR afferents. The DHS modulates the transfer function between the DR and the DC (i.e., modulates the response of axons in the DC to the DRS), and the effect of such modulation is monitored to indicate the patient's response to the DHS.

In the illustrated embodiment, the modulation control circuit 1516 includes a response input 1550 and a parameter calibrator 1551. The response input 1550 receives response information indicative of one or more responses of the patient to the DHS delivered by the modulation device 1512. In various embodiments, the response information includes one or more response parameters each being a quantitative measure of a response of the one or more responses to the DHS. In various embodiments, the response information includes one or more response parameters each indicative of a physiological function associated with pain. Examples of the one or more responses to the DHS include physiological responses such as neurological responses and cardiovascular responses, physical responses, and behavioral responses. In various embodiments, the one or more responses to the DHS may include one or more types of acute response and/or one or more types of long-term responses. The parameter calibrator 1551 adjusts one or more modulation parameters of the plurality of modulation parameters to maintain a value of each parameter of the one or more response parameters within a target range. The target range may be determined for (1) maximum positive impact on the one or more response parameters (maximum value, minimum value, or other optimal values, depending on the nature of each parameter); (2) approximately optimal pain relief when the patient's physiologic state changes (such as during the patient's posture change or disease progression); and/or (3) maximum positive impact on the patient's quality of life (which may be indicated by objective measures as well as the patient's subject feedback).

The monitoring device 1552 monitors the one or more responses to the DHS and produce the response information. In various embodiments, the monitoring device 1552 may be implemented as a totally implantable device, a partially implantable device, a portable device, a patient-wearable device, or a non-portable, depending on the nature of the one or more responses to be monitored and the available monitoring technology. In various embodiments, the monitoring device 1552 may include one or more components that are totally implantable, partially implantable, portable device, patient-wearable device, and/or non-portable, depending on the nature of the one or more responses to be monitored and the available monitoring technology.

In the illustrated embodiment, the monitoring device includes one or more sensors 1553 and a parameter generator 1554. The one or more sensors 1553 sense one or more signals, such as one or more neurophysiological signals, that indicate the patient's response to the DHS. The parameter generator 1554 derives the one or more response parameters from the sensed one or more signals. In various embodiments, the one or more sensors 1553 are used to perform various diagnostic procedures from which the one or more response parameters can be derived for used by the parameter calibrator 1551 of the modulation device 1512. Examples of such diagnostic procedures include quantitative sensory testing (QST), electroencephalography (EEG), electrocorticography (ECoG), diffuse optical imaging, and functional magnetic resonance imaging (fMRI). Examples of the one or more response parameters include sensation and pain thresholds obtained from the QST, mapping and/or mophorlogical characteristics of evoked potentials such as amplitude and latency (onset time of evoked potential after the stimulation) or power spectrum obtained from the EEG, mapping and/or mophorlogical characteristics of evoked potentials such as amplitude and latency or power spectrum obtained from the ECoG, cerebral blood flow, hemodynamics, and metabolism obtained from the diffuse optical imaging, and measure of blood flow in brain indicative of brain activity obtained from the fMRI. In one embodiment, the one or more sensors 1553 sense the one or more neurophysiological signals including local field potentials (LFPs) in axons in the DC sensed while modulation device 1512 delivers the DHS to the DH interleaved with the DRS to the DR. Examples of the one or more response parameters include one or more parameters representative of a morphology of the LFPs, such as latency (onset time of evoked response after the stimulation), amplitude, width (of a characteristic potential), and duration (the extent of time for the appearance of characteristic potentials) of the LFPs. In one embodiment, the one or more sensors 1553 sense the one or more neurophysiological signals including evoked compound action potentials (eCAPs) in axons in the DC sensed while modulation device 1512 delivers the DHS to the DH interleaved with the DRS to the DR. Examples of the one or more response parameters include one or more parameters representative of a morphology of the eCAPs, such as latency, amplitude, width, and duration of the LFPs.

In various embodiments, the monitoring device 1552 is communicatively coupled to the modulation device 1512 via a communication link 1555 to close the loop for feedback control of the DHS in the system 1510. In various embodiments, the communication link 1555 may include a wired or wireless link direct between the monitoring device 1552 and the modulation device 1512 to allow for automatic feedback control of the DHS. In various other embodiments, the communication link 1555 may include an interface that allows for automatic or semi-automatic feedback control of the DHS, depending on whether the operation of the interface requires or allows user intervention, as further discussed below with reference to FIG. 16.

Figure 16:
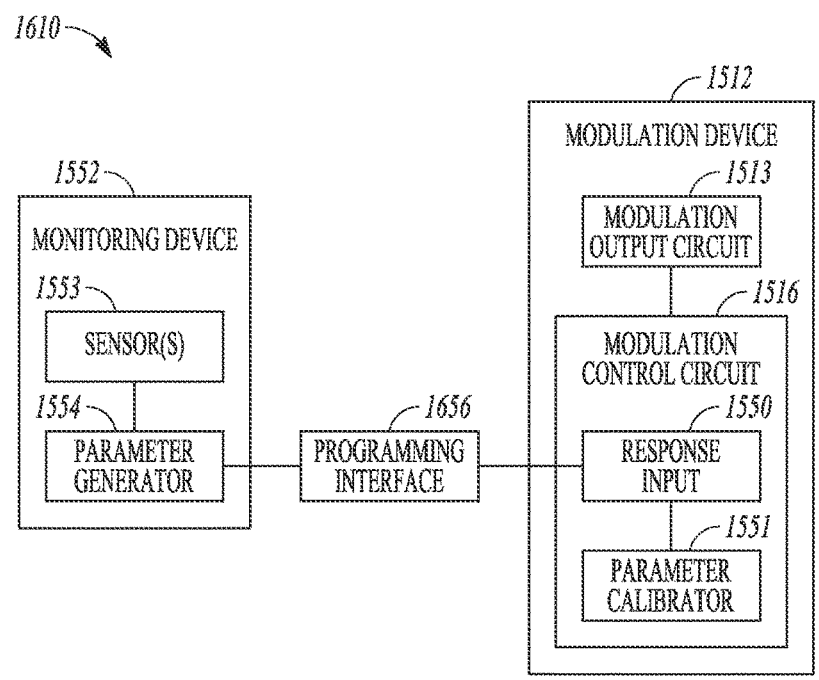
FIG. 16 illustrates, by way of example, an embodiment of another neuromodulation system for closed-loop dorsal horn stimulation.

FIG. 16 illustrates, by way of example, an embodiment of a neuromodulation system 1610 for closed-loop DHS. The system 1610 includes the system 1510 with the communication link 1555 including a programming interface 1656. In various embodiments, the programming interface 1656 translates the one or more response parameters generated by the monitoring device 1552 into one or more programming signals for the modulation device 1512, when such translation is necessary due to the nature of the monitored responses and technology available for processing the monitored responses, for example. In various embodiments, the programming interface 1656 may be implemented in the clinician's programmer (CP) 628 and/or a remote controller (RC) 627. For example, a clinician may use the CP 628 to close the loop and/or to initiate a calibration process performed by the parameter calibrator 1551, such as when the clinician reviews results from a diagnostic procedure and derives the one or more response parameters from the results. A patient may use the RC 627 to close the loop and/or to initiate a calibration process performed by the parameter calibrator 1551, such as when the patient receives an alert or other signal from the monitoring device and is allowed to decide whether the calibration process is desirable based on the current or recent experience with the DHS applied. In various other embodiments, the programming interface 1656 closes the feedback control loop, which may include the parameter translation, without necessarily an intervention from a user such as the clinician or the patient, and therefore allows for automatic feedback control of the DHS in the system 1610.

Figure 17:
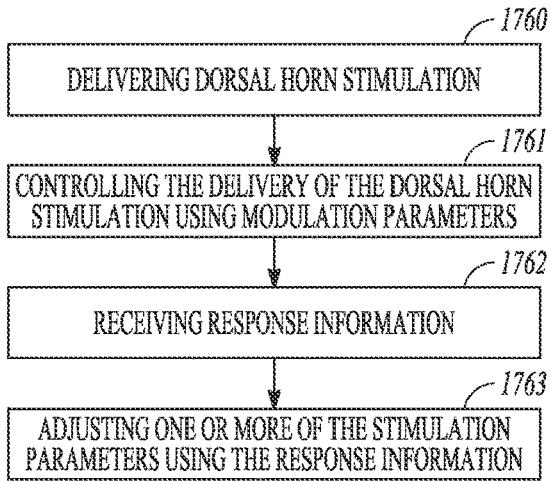
FIG. 17 illustrates, by way of example, an embodiment of a method for closed-loop dorsal horn stimulation.

FIG. 17 illustrates, by way of example, an embodiment of a method for closed-loop DHS. In one embodiment, the system 1510 or the system 1610 is used to perform the method illustrated in FIG. 17.

At 1760. DHS is delivered to the DH. In one embodiment, the DHS is delivering from an implantable device. At 1761, the delivery of the DHS is controlled by executing a neuromodulation algorithm for pain management using a plurality of modulation parameters. In one embodiment, the neuromodulation algorithm is for delivering sub-perception DHS to treat pain without causing paresthesia. The sub-perception DHS selectively stimulates the DH over the DC. At 1762, response information indicative of one or more responses to the DHS is received. At 1763, one or more modulation parameters of the plurality of modulation parameters are adjusted using the response information.

In various other embodiments, the method as illustrated in FIG. 17 may be performed automatically or semi-automatically, depending on whether user intervention is required or allowed. For example, when the response information becomes available, it may be necessary or desirable to allow a user such as a clinician or the patient to decide whether and/or how the one or more modulation parameters should be adjusted, depending on available technology and user preference.

Figure 18:
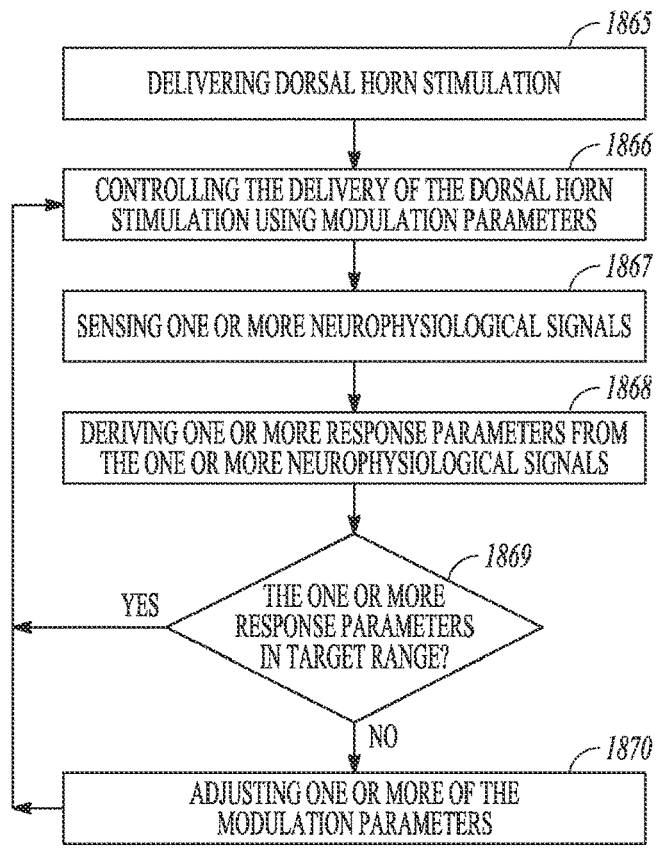
FIG. 18 illustrates, by way of example, an embodiment of a method for optimizing dorsal horn stimulation.

FIG. 18 illustrates, by way of example, an embodiment of a method for optimizing DHS. In one embodiment, the system 1510 or the system 1610 is used to perform the method illustrated in FIG. 18.

At 1865, DHS is delivered to the DH. In one embodiment, the DHS is delivering from an implantable device. At 1866, the delivery of the DHS is controlled by executing a neuromodulation algorithm for pain management using a plurality of modulation parameters. In one embodiment, the neuromodulation algorithm is for delivering sub-perception DHS to treat pain without causing paresthesia. The sub-perception DHS selectively stimulates the DH over the DC.

At 1867, one or more neurophysiological signals are sensed. The one or more neurophysiological signals are indicative of one or more responses to the DHS. Examples of the neurophysiologic signals include, but are not limited to, those sensed when performing one or more of quantitative sensory testing, EEG. ECoG, diffuse optical imaging, and fMRI.

At 1868, one or more response parameters are derived from the one or more neurophysiological signals. The one or more response parameters are each a quantitative measure of a response of the one or more responses to the DHS. In one embodiment, the one or more response parameters are each indicative of a physiological function associated with pain.

At 1869, the one or more response parameters are compared to a target range. If the one or more response parameters are within the target range, the plurality of modulation parameters continues to be used to control the delivery of the DHS at 1866 without adjustment. If the one or more response parameters fall out of the target range, one or more modulation parameter of the plurality of modulation parameters are adjusted at 1870 before they are continued to be used to control the delivery of the DHS at 1866. In various embodiments, the one or more modulation parameters of the plurality of modulation parameters are adjusted to maintain the value of each parameter of the one or more response parameters within its target range.

In various other embodiments, the method as illustrated in FIG. 18 may be performed automatically or semi-automatically, depending on whether user intervention is required or allowed. For example, when the neurophysiological signals are sensed as part of a diagnostic procedure such as the quantitative sensory testing, EEG, ECoG, diffuse optical imaging, or fMRI, a clinician's intervention may be needed to complete the procedure and/or derive the one or more response parameters.

Figure 19:
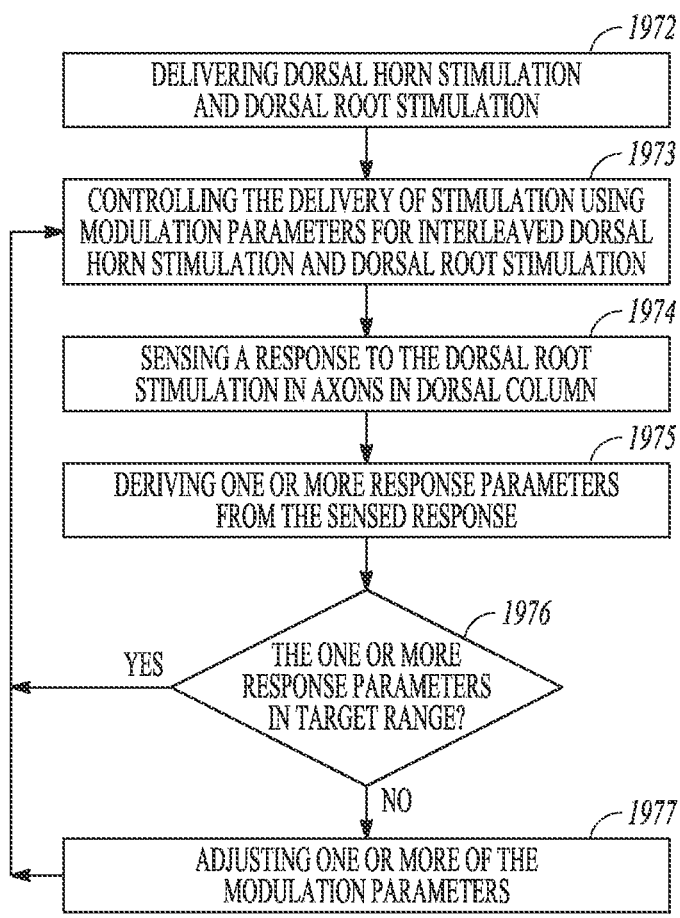
FIG. 19 illustrates, by way of example, an embodiment of another method for optimizing dorsal horn stimulation.

FIG. 19 illustrates, by way of example, an embodiment of another method for optimizing DHS. In one embodiment, the system 1510 or the system 1610 is used to perform the method illustrated in FIG. 19.

At 1972, DHS is delivered to the DH, and DRS is delivered to DR. In one embodiment, the DHS is delivering from an implantable device. At 1973, the delivery of the DHS is controlled by executing a test neuromodulation algorithm using a plurality of modulation parameters for the DHS to be interleaved with the DRS.

At 1974, a response to the DRS is sensed in axons in the DC modulated by the DHS during the delivery of the DHS interleaved with the DRS. Examples of the response include local field potentials (LFPs) and evoked compound action potentials (eCAPs), both sensed from the DC.

At 1975, one or more response parameters are derived from the sense response to the DRS. The one or more response parameters are each a quantitative measure of the modulation of the transfer function between the DR and the DC resulting from the DHS.

At 1976, the one or more response parameters are compared to a target range. If the one or more response parameters are within the target range, the plurality of modulation parameters continue to be used to control the delivery of the DHS at 1973 without adjustment. If the one or more response parameters fall out of the target range, one or more modulation parameters of the plurality of modulation parameters are adjusted at 1977 before they are continued to be used in the execution of the test neuromodulation algorithm. In various embodiments, the one or more modulation parameters of the plurality of modulation parameters are adjusted until the value of each parameter of the one or more response parameters is within its target range.

In various other embodiments, the method as illustrated in FIG. 19 may be performed automatically or semi-automatically, depending on whether user intervention is required or allowed. For example, depending on user preference, when the one or more response parameters fall out of the target range, the patient may be notified and allowed to decide whether adjustment to the one or more modulation parameters is desirable based on the patient's own perception.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for applying neuromodulation to a patient having a nervous system including a dorsal horn, a dorsal root, and a dorsal column, the system comprising:
   a modulation output circuit configured to deliver dorsal horn stimulation to the dorsal horn and to deliver dorsal root stimulation to the dorsal root; and
   a modulation control circuit configured to control the delivery of the dorsal horn stimulation and the dorsal root stimulation using a plurality of modulation parameters, wherein a neurophysiological response of the dorsal column to the dorsal root stimulation is modulated by the dorsal horn stimulation during the delivery of the dorsal horn stimulation interleaved with the dorsal root stimulation, the modulation control circuit including:
   a response input configured to receive response information including one or more response parameters derived from a sensor configured to sense a quantitative measure of the neurophysiological response of the dorsal column to the dorsal root stimulation modulated by the dorsal horn stimulation during the delivery of the dorsal horn stimulation interleaved with the dorsal root stimulation; and
   a parameter calibrator configured to adjust one or more modulation parameters of the plurality of modulation parameters using the response information.

2. The system of claim 1, wherein the parameter calibrator is configured to adjust the one or more modulation parameters of the plurality of modulation parameters to maintain the one or more response parameters within a target value range.

3. The system of claim 2, further comprising:
   a parameter generator configured to derive the one or more response parameters from the sensed neurophysiological response.

4. The system of claim 3, wherein the sensor is configured to sense local field potentials (LFPs) in axons in the dorsal column, and the parameter generator is configured to derive one or more parameters of the one or more response parameters from the sensed LFPs.

5. The system of claim 3, wherein the sensor is configured to sense evoked compound action potentials (eCAPs) in axons in the dorsal column, and the parameter generator is configured to derive one or more parameters of the one or more response parameters from the sensed eCAPs.

6. The system of claim 2, further comprising:
one or more sensors configured to sense one or more neurophysiological signals each indicative of a physiological function associated with pain; and
a parameter generator configured to derive the one or more response parameters from the one or more neurophysiological signals.

7. The system of claim 1, comprising an implantable modulation device including the modulation output circuit, the response input, and the modulation control circuit, and further comprising a monitoring device configured to monitor the neurophysiological response and produce the response information.

8. The system of claim 7, wherein the monitoring device comprises an implantable monitoring device.

9. The system of claim 7, wherein the monitoring device comprises a wearable monitoring device.

10. The system of claim 1, wherein the modulation control circuit is configured to control the delivery of the dorsal horn stimulation for sub-perception dorsal horn stimulation, the sub-perception dorsal horn stimulation to selectively stimulate the dorsal horn over the dorsal column.

11. A method for applying neuromodulation to a patient having a nervous system including a dorsal horn, a dorsal root, and a dorsal column, the method comprising:
delivering dorsal horn stimulation to the dorsal horn and dorsal root stimulation to the dorsal root;
controlling the delivery of the dorsal horn stimulation and the dorsal root stimulation using a plurality of modulation parameters such that a neurophysiological response of the dorsal column to the dorsal root stimulation is modulated by the dorsal horn stimulation during the delivery of the dorsal horn stimulation interleaved with the dorsal root stimulation;
receiving response information including one or more response parameters derived from a sensor configured to sense a quantitative measure of the neurophysiological response of the dorsal column to the dorsal root stimulation modulated by the dorsal horn stimulation during the delivery of the dorsal horn stimulation interleaved with the dorsal root stimulation; and
adjusting one or more modulation parameters of the plurality of modulation parameters using the response information.

12. The method of claim 11, further comprising:
deriving the one or more response parameters of the response information from the one or more neurophysiological signals.

13. The method of claim 12, wherein sensing the one or more neurophysiological signals comprises sensing one or more neurophysiological signals indicative of a response to the dorsal root stimulation in axons in the dorsal column modulated by the dorsal horn stimulation during the delivery of the dorsal horn stimulation interleaved with the dorsal root stimulation.

14. The method of claim 13, wherein sensing the response to the dorsal root stimulation in axons in the dorsal column comprises sensing local field potentials (LFPs) in axons in the dorsal column.

15. The method of claim 13, wherein sensing the response to the dorsal root stimulation in axons in the dorsal column comprises sensing evoked compound action potentials (eCAPs) in axons in the dorsal column.

16. The method of claim 12, wherein sensing the one or more neurophysiological signals comprising performing one or more of quantitative sensory testing, electroencephalography (EEG), electrocorticography (ECoG), diffuse optical imaging, and functional magnetic resonance imaging (fMRI).

17. The method of claim 12, wherein adjusting one or more modulation parameters of the plurality of modulation parameters comprises adjusting the one or more modulation parameters of the plurality of modulation parameters to maintain the one or more response parameters within a target value range.

18. The method of claim 12, wherein deriving the one or more response parameters comprises deriving one or more response parameters each indicative of a physiological function associated with pain.

19. The method of claim 11, wherein controlling the delivery of the dorsal horn stimulation comprises controlling the delivery of the dorsal horn stimulation for sub-perception dorsal horn stimulation, the sub-perception dorsal horn stimulation to selectively stimulate the dorsal horn over the dorsal column.

20. The method of claim 19, wherein delivering the dorsal horn stimulation and the dorsal root stimulation comprises delivering the dorsal horn stimulation and the dorsal root stimulation from an implantable device.

* * * * *